(12) United States Patent
Loeffler et al.

(10) Patent No.: US 7,195,011 B2
(45) Date of Patent: Mar. 27, 2007

(54) CONVERTIBLE FLUID FEED SYSTEM WITH COMFORMABLE RESERVOIR AND METHODS

(75) Inventors: Joseph P. Loeffler, Mountain View, CA (US); David Rapp, Mountain View, CA (US); Victor Briones, Gilroy, CA (US); Ralf Bitdinger, Palo Alto, CA (US); Michael Klimowicz, Los Altos, CA (US)

(73) Assignee: Aerogen, Inc., San Carlos, CA (US)

(*) Notice: Subject to any disclaimer, the term of this patent is extended or adjusted under 35 U.S.C. 154(b) by 157 days.

(21) Appl. No.: 10/882,888

(22) Filed: Jun. 30, 2004

(65) Prior Publication Data

US 2004/0256488 A1   Dec. 23, 2004

Related U.S. Application Data

(62) Division of application No. 09/812,987, filed on Mar. 20, 2001, now Pat. No. 6,948,491.

(51) Int. Cl.
  *A61M 11/00*   (2006.01)
  *A61M 15/00*   (2006.01)
  *B05B 7/26*   (2006.01)

(52) U.S. Cl. .............. 128/200.14; 128/200.11; 128/200.18; 128/200.21; 239/317

(58) Field of Classification Search .......... 128/200.14, 128/200.11, 200.13, 200.21, 200.24, 203.17, 128/203.26, 203.27, 204.14, 204.17, 203.16; 431/277; 222/325, 108; 239/317, 342, 350
See application file for complete search history.

(56) References Cited

U.S. PATENT DOCUMENTS

| | | | |
|---|---|---|---|
| 550,315 A | 11/1895 | Allen | 215/6 |
| 809,159 A | 1/1906 | Willis et al. | |
| 1,680,616 A | 8/1928 | Horst | 215/6 |
| 2,022,520 A | 11/1935 | Philbrick | |
| 2,101,304 A | 12/1937 | Wright | 120/50 |
| 2,158,615 A | 5/1939 | Wright | 120/50 |

(Continued)

FOREIGN PATENT DOCUMENTS

CH   477 885   10/1969

(Continued)

OTHER PUBLICATIONS

Heyder, J. et al., "Deposition of particles in the human respiratory tract in the size range 0.005-15 microns." J Aerosol Sci 17: 811-825, 1986.

(Continued)

*Primary Examiner*—Teena Mitchell
*Assistant Examiner*—Annette Dixon
(74) *Attorney, Agent, or Firm*—Townsend and Townsend and Crew LLP

(57) ABSTRACT

A feed system for an aerosolizer utilizes an ampoule containing a liquid and includes a housing having an ampoule region into which the ampoule is held, and a liquid receiving region that is adapted to receive liquid dispensed from the ampoule. An interface is used to couple the liquid receiving region to an aerosol generator, whereby liquid from the liquid receiving region is permitted to flow to the aerosol generator for aerosolization.

16 Claims, 10 Drawing Sheets

U.S. PATENT DOCUMENTS

| | | | |
|---|---|---|---|
| 2,187,528 A | 1/1940 | Wing | 120/50 |
| 2,223,541 A | 12/1940 | Baker | 120/50 |
| 2,266,706 A | 12/1941 | Fox et al. | 128/173 |
| 2,283,333 A | 5/1942 | Martin | 120/50 |
| 2,292,381 A | 8/1942 | Klagges | 120/50 |
| 2,360,297 A | 10/1944 | Wing | 120/52 |
| 2,375,770 A | 5/1945 | Dahlberg | 120/52 |
| 2,383,098 A | 8/1945 | Wheaton | |
| 2,404,063 A | 7/1946 | Healy | 120/51 |
| 2,430,023 A | 11/1947 | Longmaid | 120/52 |
| 2,474,996 A | 7/1949 | Wallis | 120/52 |
| 2,512,004 A | 6/1950 | Wing | 120/52 |
| 2,521,657 A | 9/1950 | Severy | 120/50 |
| 2,681,041 A | 6/1954 | Zodtner et al. | 120/50 |
| 2,705,007 A | 3/1955 | Gerber | |
| 2,735,427 A | 2/1956 | Sullivan | |
| 2,764,979 A | 10/1956 | Henderson | |
| 2,779,623 A | 1/1957 | Elisenkraft | 299/1 |
| 2,935,970 A | 5/1960 | Morse et al. | 120/52 |
| 3,103,310 A | 9/1963 | Lang | |
| 3,325,031 A | 6/1967 | Singier | 215/6 |
| 3,411,854 A | 11/1968 | Rosler et al. | 401/227 |
| 3,515,348 A | 6/1970 | Coffman, Jr. | |
| 3,550,864 A | 12/1970 | East | |
| 3,558,052 A | 1/1971 | Dunn | 293/3 |
| 3,561,444 A | 2/1971 | Boucher | |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | 239/102 |
| 3,771,982 A | 11/1973 | Dobo | |
| 3,790,079 A | 2/1974 | Berglund et al. | 239/3 |
| 3,804,329 A | 4/1974 | Martner | 239/4 |
| 3,812,854 A | 5/1974 | Michaels et al. | 128/194 |
| 3,838,686 A | 10/1974 | Szekely | |
| 3,842,833 A | 10/1974 | Ogle | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | 222/206 |
| 3,950,760 A | 4/1976 | Ilse-dore Stromberger et al. | 346/140 |
| 3,951,313 A | 4/1976 | Coniglione | 222/186 |
| 3,958,249 A | 5/1976 | DeMaine et al. | 346/1 |
| 3,970,250 A | 7/1976 | Drews | |
| 3,983,740 A | 10/1976 | Danel | 73/12 |
| 3,993,223 A | 11/1976 | Welker, III et al. | 222/107 |
| 4,005,435 A | 1/1977 | Lundquist et al. | 346/1 |
| 4,030,492 A | 6/1977 | Simburner | |
| 4,052,986 A | 10/1977 | Scaife | 128/260 |
| 4,059,384 A | 11/1977 | Holland et al. | |
| D246,574 S | 12/1977 | Meierhoefer | D9/67 |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | 215/6 |
| 4,106,503 A | 8/1978 | Rsenthal et al. | |
| 4,109,174 A | 8/1978 | Hodgson | |
| 4,113,809 A | 9/1978 | Abair et al. | |
| D249,958 S | 10/1978 | Meierhoefer | D24/56 |
| 4,119,096 A | 10/1978 | Drews | 128/194 |
| 4,121,583 A | 10/1978 | Chen | |
| 4,159,803 A | 7/1979 | Cameto et al. | 239/102 |
| 4,190,052 A * | 2/1980 | McCarthy | 607/84 |
| 4,207,990 A | 6/1980 | Weiler et al. | |
| 4,210,155 A | 7/1980 | Grimes | |
| 4,226,236 A | 10/1980 | Genese | 604/89 |
| 4,240,081 A | 12/1980 | Devitt | 346/75 |
| 4,240,417 A | 12/1980 | Holever | |
| 4,248,227 A | 2/1981 | Thomas | |
| 4,261,512 A | 4/1981 | Zierenberg | 239/102 |
| D259,213 S | 5/1981 | Pagels | D9/370 |
| 4,268,460 A | 5/1981 | Boiarski et al. | 261/1 |
| 4,294,407 A | 10/1981 | Reichl et al. | 239/102 |
| 4,298,045 A | 11/1981 | Weiler et al. | 150/0.5 |
| 4,299,784 A | 11/1981 | Hense | |
| 4,300,546 A | 11/1981 | Kruber | 128/200 |
| 4,301,093 A | 11/1981 | Eck | 261/1 |
| 4,319,155 A | 3/1982 | Makai et al. | |
| 4,334,531 A | 6/1982 | Reichl et al. | 128/200.14 |
| 4,336,544 A | 6/1982 | Donald et al. | 346/1.1 |
| 4,338,576 A | 7/1982 | Takahashi et al. | 331/67 |
| 4,368,476 A | 1/1983 | Uehara et al. | 346/140 R |
| 4,368,850 A | 1/1983 | Szekely | |
| 4,374,707 A | 2/1983 | Pollack | |
| 4,389,071 A | 6/1983 | Johnson, Jr. et al. | 299/14 |
| 4,408,719 A | 10/1983 | Last | 239/102 |
| 4,428,802 A | 1/1984 | Kanai et al. | |
| 4,431,136 A | 2/1984 | Janner et al. | 239/102 |
| 4,454,877 A | 6/1984 | Miller et al. | 128/200.21 |
| 4,465,234 A | 8/1984 | Maehara et al. | 239/102 |
| 4,474,251 A | 10/1984 | Johnson, Jr. | 175/67 |
| 4,474,326 A | 10/1984 | Takahashi | 239/102 |
| 4,475,113 A | 10/1984 | Lee et al. | 346/1.1 |
| 4,479,609 A | 10/1984 | Maeda et al. | 239/102 |
| 4,512,341 A | 4/1985 | Lester | |
| 4,530,464 A | 7/1985 | Yamamoto et al. | 239/102 |
| 4,533,082 A | 8/1985 | Maehara et al. | 239/102 |
| 4,539,575 A | 9/1985 | Nilsson | 346/140 R |
| 4,544,933 A | 10/1985 | Heinzl | 346/140 R |
| 4,546,361 A | 10/1985 | Brescia et al. | 346/140 R |
| 4,550,325 A | 10/1985 | Viola | 346/140 R |
| 4,566,452 A | 1/1986 | Farr | |
| 4,591,883 A | 5/1986 | Isayama | 346/140 R |
| 4,593,291 A | 6/1986 | Howkins | 346/1.1 |
| 4,605,167 A | 8/1986 | Maehara | 239/102 |
| 4,613,326 A | 9/1986 | Szwarc | |
| 4,620,201 A | 10/1986 | Heinzl et al. | 346/140 R |
| 4,628,890 A | 12/1986 | Freeman | 123/593 |
| 4,632,311 A | 12/1986 | Nakane et al. | 239/101 |
| 4,658,269 A | 4/1987 | Rezanka | |
| 4,659,014 A | 4/1987 | Soth et al. | 239/102.2 |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | 239/589.1 |
| 4,693,853 A | 9/1987 | Falb et al. | 261/39.1 |
| 4,702,418 A | 10/1987 | Carter et al. | 239/101 |
| 4,722,906 A | 2/1988 | Guire | 436/501 |
| 4,753,579 A | 6/1988 | Murphy | 417/322 |
| 4,790,479 A | 12/1988 | Matsumoto et al. | 239/102.2 |
| 4,793,339 A | 12/1988 | Matsumoto et al. | 128/200.16 |
| 4,796,807 A | 1/1989 | Bendig et al. | 239/102.2 |
| 4,799,622 A | 1/1989 | Ishikawa et al. | 239/102.2 |
| 4,805,609 A | 2/1989 | Roberts et al. | |
| 4,819,629 A | 4/1989 | Jonson | |
| 4,819,834 A | 4/1989 | Thiel | |
| 4,826,080 A | 5/1989 | Ganser | |
| 4,826,759 A | 5/1989 | Guire et al. | 435/4 |
| 4,828,886 A | 5/1989 | Hieber | 427/422 |
| 4,843,445 A | 6/1989 | Stemme | |
| 4,849,303 A | 7/1989 | Graham et al. | |
| 4,850,534 A | 7/1989 | Takahashi et al. | 239/102.2 |
| 4,865,006 A | 9/1989 | Nogi et al. | 123/590 |
| 4,871,489 A | 10/1989 | Ketcham | |
| 4,872,553 A | 10/1989 | Suzuki et al. | 206/524.4 |
| 4,877,989 A | 10/1989 | Drews et al. | 310/323 |
| 4,888,516 A | 12/1989 | Daeges et al. | 310/323 |
| 4,922,901 A | 5/1990 | Brooks et al. | |
| 4,926,915 A | 5/1990 | Deussen et al. | 141/290 |
| 4,934,358 A | 6/1990 | Nilsson et al. | 128/200.23 |
| 4,954,225 A | 9/1990 | Bakewell | |
| 4,957,239 A | 9/1990 | Tempelman | |
| 4,964,521 A | 10/1990 | Wieland et al. | |

| | | | | | |
|---|---|---|---|---|---|
| D312,209 S | 11/1990 | Morrow et al. ............... D9/371 | 5,383,906 A | 1/1995 | Burchett et al. ............. 606/236 |
| 4,968,299 A | 11/1990 | Ahlstrand et al. ............. 604/90 | 5,388,571 A | 2/1995 | Roberts et al. |
| 4,971,665 A | 11/1990 | Sexton | 5,392,769 A | 2/1995 | Johansson et al. |
| 4,973,493 A | 11/1990 | Guire ............................ 427/2 | 5,396,883 A | 3/1995 | Knupp et al. |
| 4,976,259 A | 12/1990 | Higson et al. ......... 128/200.18 | 5,414,075 A | 5/1995 | Swan et al. ................. 568/333 |
| 4,979,959 A | 12/1990 | Guire ......................... 623/66 | 5,415,161 A | 5/1995 | Ryder .................... 128/200.23 |
| 4,994,043 A | 2/1991 | Ysebaert ....................... 604/90 | 5,419,315 A | 5/1995 | Rubsamen |
| 5,002,048 A | 3/1991 | Makiej, Jr. | 5,426,458 A | 6/1995 | Wenzel et al. |
| 5,002,582 A | 3/1991 | Guire et al. .................. 623/66 | 5,431,155 A | 7/1995 | Marelli ....................... 128/200 |
| 5,007,419 A | 4/1991 | Weinstein et al. | 5,435,282 A | 7/1995 | Haber et al. ........... 128/200.16 |
| 5,016,024 A | 5/1991 | Lam et al. | 5,435,297 A | 7/1995 | Klein |
| 5,021,701 A | 6/1991 | Takahashi et al. .......... 310/345 | 5,437,267 A | 8/1995 | Weinstein et al. |
| 5,022,587 A | 6/1991 | Hochstein | 5,445,141 A | 8/1995 | Kee et al. |
| 5,024,733 A | 6/1991 | Abys et al. | D362,390 S | 9/1995 | Weiler ......................... D9/520 |
| 5,046,627 A | 9/1991 | Hansen | 5,449,502 A | 9/1995 | Igusa et al. |
| 5,062,419 A | 11/1991 | Rider | 5,452,711 A | 9/1995 | Gault .................... 128/200.14 |
| 5,063,396 A | 11/1991 | Shiokawa et al. ...... 346/140 R | 5,458,135 A | 10/1995 | Patton et al. ........... 128/200.14 |
| 5,063,922 A | 11/1991 | Hakkinen ............... 128/200.16 | 5,458,289 A | 10/1995 | Cater |
| 5,073,484 A | 12/1991 | Swanson et al. ........... 435/7.92 | 5,474,059 A | 12/1995 | Cooper |
| 5,076,266 A | 12/1991 | Babaev .................. 128/200.16 | 5,477,992 A | 12/1995 | Jinks et al. ............... 222/402.2 |
| 5,078,976 A * | 1/1992 | Shibauchi et al. ........... 422/298 | 5,479,920 A | 1/1996 | Piper et al. |
| 5,080,093 A | 1/1992 | Raabe et al. | 5,487,378 A | 1/1996 | Robertson et al. ..... 128/200.16 |
| 5,080,649 A | 1/1992 | Vetter .......................... 604/191 | 5,489,266 A | 2/1996 | Grimard ...................... 604/82 |
| 5,086,765 A | 2/1992 | Levine | 5,497,944 A | 3/1996 | Weston et al. |
| 5,086,785 A | 2/1992 | Gentile et al. | D369,212 S | 4/1996 | Snell ......................... D24/117 |
| 5,115,803 A | 5/1992 | Sioutas .................. 128/200.23 | 5,511,726 A | 4/1996 | Greenspan et al. |
| 5,115,971 A | 5/1992 | Greenspan et al. | 5,512,329 A | 4/1996 | Guire ......................... 427/508 |
| D327,008 S | 6/1992 | Friedman .................... D9/521 | 5,512,474 A | 4/1996 | Clapper et al. ........ 435/240.243 |
| 5,118,040 A * | 6/1992 | Abe ........................ 239/284.1 | 5,515,841 A | 5/1996 | Robertson et al. ..... 128/200.16 |
| 5,122,116 A | 6/1992 | Kriesel et al. ................ 604/89 | 5,515,842 A | 5/1996 | Lamseyev et al. ..... 128/200.18 |
| 5,129,579 A | 7/1992 | Conte | 5,516,043 A | 5/1996 | Manna et al. |
| 5,134,993 A | 8/1992 | Van Der Linden et al. | 5,518,179 A | 5/1996 | Humberstone et al. .. 239/102.2 |
| 5,139,016 A | 8/1992 | Waser ................... 128/200.16 | 5,529,055 A | 6/1996 | Gueret .................. 128/200.16 |
| 5,140,740 A | 8/1992 | Weigelt | 5,533,497 A | 7/1996 | Ryder .................... 128/200.21 |
| 5,147,073 A | 9/1992 | Cater | 5,542,410 A | 8/1996 | Goodman et al. |
| 5,152,456 A | 10/1992 | Ross et al. ................. 239/102.2 | 5,549,102 A | 8/1996 | Lintl et al. |
| 5,157,372 A | 10/1992 | Langford | 5,560,837 A | 10/1996 | Trueba |
| 5,164,740 A | 11/1992 | Irvi ............................ 346/1.1 | 5,563,056 A | 10/1996 | Swan et al. ................. 435/180 |
| 5,169,029 A | 12/1992 | Behar et al. | D375,352 S | 11/1996 | Bologna .................... D24/115 |
| 5,170,782 A | 12/1992 | Kocinski ............... 128/200.16 | 5,579,757 A | 12/1996 | McMahon et al. ..... 128/200.21 |
| 5,180,482 A | 1/1993 | Abys et al. .................. 205/224 | 5,582,330 A | 12/1996 | Iba .............................. 222/212 |
| 5,186,164 A | 2/1993 | Raghurprasad ........ 128/200.14 | 5,584,285 A | 12/1996 | Salter et al. |
| 5,186,166 A | 2/1993 | Riggs et al. ........... 128/203.15 | 5,586,550 A | 12/1996 | Ivri et al. ............... 128/200.16 |
| 5,198,157 A | 3/1993 | Bechet .......................... 264/9 | 5,588,166 A | 12/1996 | Burnett |
| 5,201,322 A | 4/1993 | Henry et al. | 5,601,077 A | 2/1997 | Imbert |
| 5,213,860 A | 5/1993 | Laing | 5,609,798 A | 3/1997 | Liu et al. |
| 5,217,148 A | 6/1993 | Cater | 5,632,878 A | 5/1997 | Kitano |
| 5,217,492 A | 6/1993 | Guire et al. .................. 623/11 | 5,635,096 A | 6/1997 | Singer et al. |
| 5,227,168 A | 7/1993 | Chvapil | 5,637,460 A | 6/1997 | Swan et al. ..................... 435/6 |
| 5,230,496 A | 7/1993 | Shillington et al. | 5,647,349 A | 7/1997 | Ohki et al. |
| 5,245,995 A | 9/1993 | Sullivan et al. | 5,653,227 A | 8/1997 | Barnes et al. |
| 5,248,087 A | 9/1993 | Dressler | 5,654,007 A | 8/1997 | Johnson et al. ............. 424/489 |
| 5,258,041 A | 11/1993 | Guire et al. .................. 623/66 | 5,654,162 A | 8/1997 | Guire et al. ................ 435/7.92 |
| 5,261,601 A | 11/1993 | Ross et al. ................. 239/102.2 | 5,654,460 A | 8/1997 | Rong ........................ 556/472 |
| 5,263,992 A | 11/1993 | Guire ......................... 623/66 | 5,657,926 A | 8/1997 | Toda |
| 5,279,568 A | 1/1994 | Cater | 5,660,166 A | 8/1997 | Lloyd |
| 5,297,734 A | 3/1994 | Toda ....................... 239/102.2 | 5,664,557 A | 9/1997 | Makiej, Jr. |
| 5,299,739 A | 4/1994 | Takahashi et al. ....... 239/102.2 | 5,664,706 A | 9/1997 | Cater |
| 5,303,854 A | 4/1994 | Cater | 5,665,068 A | 9/1997 | Takamura .................. 604/191 |
| 5,309,135 A | 5/1994 | Langford | 5,666,946 A | 9/1997 | Langenback |
| 5,312,281 A | 5/1994 | Takahashi et al. ............ 446/25 | 5,670,999 A | 9/1997 | Takeuchi et al. |
| 5,313,955 A | 5/1994 | Rodder | 5,685,491 A | 11/1997 | Marks et al. |
| 5,319,971 A | 6/1994 | Osswald et al. | 5,692,644 A | 12/1997 | Gueret ......................... 222/80 |
| 5,320,603 A | 6/1994 | Vetter et al. .................. 604/89 | 5,707,818 A | 1/1998 | Chudzik et al. ........... 435/7.93 |
| 5,322,057 A | 6/1994 | Raabe et al. | 5,709,202 A | 1/1998 | Lloyd et al. |
| 5,342,011 A | 8/1994 | Short ......................... 248/318 | 5,714,360 A | 2/1998 | Swan et al. ................. 435/174 |
| 5,342,504 A | 8/1994 | Hirano et al. | 5,714,551 A | 2/1998 | Bezwada et al. ............ 525/411 |
| 5,347,998 A | 9/1994 | Hodson et al. ........ 128/200.23 | 5,718,222 A | 2/1998 | Lloyd et al. ........... 128/200.14 |
| 5,348,189 A | 9/1994 | Cater | D392,184 S | 3/1998 | Weiler ......................... D9/302 |
| 5,350,116 A | 9/1994 | Cater | 5,724,957 A | 3/1998 | Rubsamen et al. |
| 5,355,872 A | 10/1994 | Riggs et al. | 5,744,515 A | 4/1998 | Clapper ....................... 523/113 |
| 5,357,946 A | 10/1994 | Kee et al. | 5,752,502 A | 5/1998 | King |
| 5,372,126 A | 12/1994 | Blau | 5,755,218 A | 5/1998 | Johansson et al. |

| | | | | | | |
|---|---|---|---|---|---|---|
| 5,758,637 A | 6/1998 | Ivri et al. ............... 128/200.16 | | 6,328,030 B1 | 12/2001 | Kidwell et al. |
| 5,775,506 A | 7/1998 | Grabenkort | | 6,328,033 B1 | 12/2001 | Avrahami |
| 5,778,459 A * | 7/1998 | Guerin ........................ 4/225.1 | | 6,341,732 B1 | 1/2002 | Martin et al. |
| 5,788,665 A | 8/1998 | Sekins | | 6,358,058 B1 | 3/2002 | Strupat et al. |
| 5,788,819 A | 8/1998 | Onishi et al. | | 6,394,363 B1 | 5/2002 | Arnott et al. |
| 5,790,151 A | 8/1998 | Mills | | 6,402,046 B1 | 6/2002 | Loser |
| 5,810,004 A | 9/1998 | Ohki et al. | | 6,405,934 B1 | 6/2002 | Hess et al. |
| 5,819,730 A | 10/1998 | Stone et al. ........... 128/203.21 | | 6,427,682 B1 | 8/2002 | Klimowicz et al. |
| 5,823,179 A | 10/1998 | Grychowski et al. | | 6,443,146 B1 | 9/2002 | Voges |
| 5,823,428 A | 10/1998 | Humberstone et al. | | 6,443,366 B1 | 9/2002 | Hirota et al. |
| 5,829,723 A | 11/1998 | Brunner et al. | | 6,467,476 B1 | 10/2002 | Ivri et al. |
| 5,836,515 A | 11/1998 | Fonzes | | 6,530,370 B1 | 3/2003 | Heinonen |
| 5,839,617 A | 11/1998 | Cater et al. | | 6,540,153 B1 | 4/2003 | Ivri |
| 5,842,468 A | 12/1998 | Denyer et al. | | 6,540,154 B1 | 4/2003 | Ivri et al. |
| 5,865,171 A | 2/1999 | Cinquin | | 6,543,443 B1 | 4/2003 | Klimowicz et al. |
| 5,878,900 A | 3/1999 | Hansen | | 6,546,927 B2 | 4/2003 | Litherland et al. |
| 5,893,515 A | 4/1999 | Hahn et al. ..................... 239/7 | | 6,550,472 B2 | 4/2003 | Litherland et al. |
| 5,894,841 A | 4/1999 | Voges | | 6,554,201 B2 | 4/2003 | Klimowicz et al. |
| 5,897,008 A | 4/1999 | Hansen | | 6,615,824 B2 | 9/2003 | Power |
| 5,910,698 A | 6/1999 | Yagi | | 6,629,646 B1 | 10/2003 | Ivri |
| 5,915,377 A | 6/1999 | Coffee | | 6,640,804 B2 | 11/2003 | Ivri |
| 5,918,637 A | 7/1999 | Fleischman | | 6,651,650 B1 | 11/2003 | Yamamoto et al. |
| 5,925,019 A | 7/1999 | Ljungquist .................. 604/191 | | 6,732,944 B2 | 5/2004 | Litherland et al. |
| 5,938,117 A | 8/1999 | Ivri ............................... 239/4 | | 6,755,189 B2 | 6/2004 | Ivri et al. |
| 5,950,619 A | 9/1999 | Van Der Linden et al. ................... 128/200.16 | | 6,769,626 B1 | 8/2004 | Haveri |
| | | | | 6,782,886 B2 | 8/2004 | Narayan et al. |
| 5,954,268 A | 9/1999 | Joshi et al. ................... 239/34 | | 6,814,071 B2 | 11/2004 | Klimowicz et al. |
| 5,960,792 A | 10/1999 | Lloyd et al. | | 6,845,770 B2 | 1/2005 | Klimowicz et al. |
| 5,964,417 A | 10/1999 | Amann et al. | | 6,851,626 B2 | 2/2005 | Patel et al. |
| 5,970,974 A | 10/1999 | Van Der Linden et al. ................... 128/200.16 | | 6,860,268 B2 | 3/2005 | Bohn et al. |
| | | | | 2001/0013554 A1 | 8/2001 | Borland et al. |
| 5,976,344 A | 11/1999 | Abys et al. | | 2001/0015737 A1 | 8/2001 | Truninger et al. |
| 5,993,805 A | 11/1999 | Sutton et al. | | 2002/0011247 A1 | 1/2002 | Ivri et al. |
| 6,007,518 A | 12/1999 | Kriesel et al. ............... 604/131 | | 2002/0104530 A1 | 8/2002 | Ivri et al. |
| 6,012,450 A | 1/2000 | Rubsamen ............. 128/200.14 | | 2002/0121274 A1 | 9/2002 | Borland et al. |
| 6,014,970 A | 1/2000 | Ivri et al. ............... 128/200.16 | | 2002/0134372 A1 | 9/2002 | Loeffler et al. |
| 6,026,809 A | 2/2000 | Abrams et al. | | 2002/0134374 A1 | 9/2002 | Loeffler et al. |
| 6,032,665 A | 3/2000 | Psaros | | 2002/0134375 A1 | 9/2002 | Loeffler et al. |
| 6,037,587 A | 3/2000 | Dowell et al. | | 2002/0134377 A1 | 9/2002 | Loeffler et al. |
| 6,045,215 A | 4/2000 | Coulman | | 2002/0162551 A1 | 11/2002 | Litherland |
| 6,045,874 A | 4/2000 | Himes ........................ 427/424 | | 2003/0140921 A1 | 7/2003 | Smith et al. |
| 6,047,818 A | 4/2000 | Warby et al. | | 2003/0150445 A1 | 8/2003 | Power et al. |
| 6,055,869 A | 5/2000 | Stemme et al. | | 2003/0150446 A1 | 8/2003 | Patel et al. |
| 6,060,128 A | 5/2000 | Kim et al. | | 2003/0226906 A1 | 12/2003 | Ivri |
| 6,062,212 A | 5/2000 | Davison et al. ........ 128/200.16 | | 2004/0000598 A1 | 1/2004 | Ivri |
| 6,068,148 A | 5/2000 | Weiler | | 2004/0004133 A1 | 1/2004 | Ivri et al. |
| 6,085,740 A | 7/2000 | Ivri et al. ............... 128/200.23 | | 2004/0035490 A1 | 2/2004 | Power |
| 6,096,011 A | 8/2000 | Trombley, III et al. ..... 604/256 | | 2004/0050947 A1 | 3/2004 | Power et al. |
| 6,105,877 A | 8/2000 | Coffee | | 2004/0139963 A1 | 7/2004 | Ivri et al. |
| 6,106,504 A | 8/2000 | Urrutia ........................ 604/251 | | 2004/0139968 A1 | 7/2004 | Loeffler et al. |
| 6,116,234 A | 9/2000 | Genova et al. | | 2004/0188534 A1 | 9/2004 | Litherland et al. |
| 6,123,413 A | 9/2000 | Agarwal et al. | | 2005/0011514 A1 | 1/2005 | Power et al. |
| 6,139,674 A | 10/2000 | Markham et al. | | | | |
| 6,142,146 A | 11/2000 | Abrams et al. | | FOREIGN PATENT DOCUMENTS | | |
| 6,145,963 A | 11/2000 | Pidwerbecki et al. | | CH | 555 681 | 9/1974 |
| 6,146,915 A | 11/2000 | Pidwerbecki et al. | | DE | 1728597 B * | 1/1978 |
| 6,152,130 A | 11/2000 | Abrams et al. | | EP | 0 049 636 A1 | 4/1982 |
| 6,155,676 A | 12/2000 | Etheridge et al. | | EP | 0 103 161 A2 | 3/1984 |
| 6,158,431 A | 12/2000 | Poole | | EP | 0 134 847 A1 | 3/1985 |
| 6,161,536 A | 12/2000 | Redmon et al. | | EP | 0 178 925 | 4/1986 |
| 6,163,588 A | 12/2000 | Matsumoto et al. | | EP | 0 387 222 A1 | 3/1990 |
| 6,182,662 B1 | 2/2001 | McGhee | | EP | 0 432 992 A1 | 6/1991 |
| 6,186,141 B1 | 2/2001 | Pike et al. | | EP | 0 480 615 A1 | 4/1992 |
| 6,196,218 B1 | 3/2001 | Voges | | EP | 0 516 565 A1 | 5/1992 |
| 6,196,219 B1 | 3/2001 | Hess et al. | | EP | 0 510 648 A2 | 10/1992 |
| 6,205,999 B1 | 3/2001 | Ivri et al. ............... 128/200.22 | | EP | 0 542 723 A2 | 5/1993 |
| 6,216,916 B1 | 4/2001 | Maddox et al. | | EP | 0 476 991 B1 | 3/1995 |
| 6,223,746 B1 | 5/2001 | Jewett et al. | | EP | 0 933 138 A2 | 4/1999 |
| 6,235,177 B1 | 5/2001 | Borland et al. ............... 205/67 | | EP | 0 923 957 A1 | 6/1999 |
| 6,254,219 B1 | 7/2001 | Agarwal et al. | | EP | 1 142 600 A1 | 10/2001 |
| 6,270,473 B1 | 8/2001 | Schwebel | | FR | 2 692 569 A1 | 6/1992 |
| 6,273,342 B1 | 8/2001 | Terada et al. | | GB | 973458 | 10/1964 |
| 6,318,640 B1 | 11/2001 | Coffee | | | | |

| | | |
|---|---|---|
| GB | 1454597 | 11/1976 |
| GB | 2 073 616 A | 10/1981 |
| GB | 2 101 500 | 1/1983 |
| GB | 2 177 623 A | 1/1987 |
| GB | 2 240 494 A | 8/1991 |
| GB | 2 272 389 A | 5/1994 |
| GB | 2 279 571 A | 1/1995 |
| JP | 57-23852 | 2/1982 |
| JP | 57-105608 | 7/1982 |
| JP | 58-61857 | 4/1983 |
| JP | 58-139757 | 8/1983 |
| JP | 59-142163 A | 8/1984 |
| JP | 60-4714 (A) | 1/1985 |
| JP | 61-8357 (A) | 1/1986 |
| JP | 61-215059 (A) | 9/1986 |
| JP | 2-135169 | 5/1990 |
| JP | 2-189161 | 7/1990 |
| JP | 60-07721 | 1/1994 |
| JP | 2000002991 A  * | 6/1998 |
| WO | WO 92/07600 | 5/1992 |
| WO | WO 92/11050 | 7/1992 |
| WO | WO92/17231 | 10/1992 |
| WO | WO 93/01404 | 1/1993 |
| WO | WO 93/010910 A1 | 6/1993 |
| WO | WO 94/09912 A1 | 5/1994 |
| WO | WO 96/09229 | 9/1996 |
| WO | WO 99/17888 | 4/1999 |
| WO | WO 99/63946 | 12/1999 |
| WO | WO 00/37132 | 6/2000 |

OTHER PUBLICATIONS

Siemens, "Servo Ultra Nebulizer 345 Operating Manual," pp. 1-23.
Berglund, R.N., et al. Generation of Monodisperse Aerosol Standards. Environ. Sci. Technology 7:2:147 (1973).
Allen, T. Particle Size Measurement. Chapman and Hall pp. 167-169 (1981).
Ueha, S., et al. Mechanism of Ultrasonic Atomization Using a Multi-Pinhole Plate. J. Acoust. Soc. Jpn. (E) 6,1:21 (1985).
Maehara, N., et al. Influence of the Vibrating System of a Multipinhole-plate Ultrasoic Nebulizer on Its Performan Review of Scientific Instruments, 57 (11), Nov. 1986, pp. 2870-2876.
Maehara, N., et al. Optimum Design Procedure for Multi-Pinhole-plate Ultrasonic Atomizer. Japanese Journal of Applied Physics, 26:215 (1987).
Ashgriz, N., et al. Development of a Controlled Spray Generator. Rev. Sci. Instrum. 58(7):1291 (1987).
Hikayama, H., et al. Ultrasonic Atomizer with Pump Function. Tech. Rpt. IEICE Japan US88-74:25 (1988).
J. Acoustical Soc. Japan 44:2:116 (1988).
J. Acoustical Soc. Japan 44:6:425 (1988).
Siemens AG, 1989, "Ink-Jet Printing: The Present State of the Art," by Wolfgang R. Wehl.
TSI Incorporated product catalog. Vibrating Orifice Aerosol Generator (1989).
Gasier Tool Company catalog, pp. 26, 29-30(19__).
Nogi, T., et al. Mixture Formation of Fuel Injection System in Gasoline Engine. Nippon Kikai Gakkai Zenkoku Taikai koenkai Koen Ronbunshu 69:660 (1991).
D.C. Cipolla et al., "Assessment of Aerosol Delivery systems for Recombinant Human Deoxyribonuclease," *S.T.P Pharma Sciences* 4 (1) 50-62, 1994.
D.C. Cipolla et al., "Characterization of Aerosols of Human Recombinant Deoxyribonuclease I (rhDNase) General by Jet Nebulizers," *Pharmaceutical Research* II (4) 491-498, 1994.
I. Gonda, "Therapeutic Aerosols," *Pharmaceutics, The Sci, of Dosage Form Design*, M.E. Aulton, 341-358, 1988.
Anthony J. Hickey, "Pharmaceutical Inhalation Aerosol Technology," *Drugs and The Pharmaceutical Sciences*, (5 172-173.
J.A. Abys et al., "Annealing Behavior of Palladium-Nickel All Electrodeposits," pp. 1-7.
"Palla Tech Pd and Pd Alloy Processes—Procedure for the Analysis of Additive IVS in Palla Tech Plating Solutions HPLC," *Technical Bulletin*, Electroplating Chemicals & Services, 029-A, Lucent Technologies, pp. 1-5, 1996.

* cited by examiner

CONVERTIBLE FLUID FEED SYSTEM WITH COMFORMABLE RESERVOIR AND METHODS

BACKGROUND OF THE INVENTION

This invention relates generally to the field of liquid aerosolization, and in particular to the management of liquids used in the aerosolization process. More specifically, the invention relates to liquid feed systems and methods for transferring liquids to an aerosol generator for aerosolization.

The ability to aerosolize or nebulize small liquid droplets is important to a variety of industries. Merely by way of example, many pharmaceuticals can now be delivered to the lungs in liquid form. Aerosolization is also a useful technique to dispense deodorizers, perfumes, insecticides or the like into the atmosphere.

Aerosolizers or nebulizers typically utilize a supply of liquid that is contained in some type of reservoir, such as a container, canister, or the like. In this way, the liquid may be stored in a sealed environment until ready for aerosolization. However, because the liquid is sealed within a container, the liquid needs to be removed and transferred to the aerosol generator prior to aerosolization. Hence, this invention relates to the use of various liquid feed systems that may be used to transfer liquids from sealed containers to an aerosol generator.

BRIEF SUMMARY OF THE INVENTION

In one embodiment, the invention provides a feed system for an aerosolizer. The feed system is used with an ampoule containing a liquid and includes a housing having an ampoule region into which the ampoule is held, and a liquid receiving region that is adapted to receive liquid dispensed from the ampoule. An interface is provided to couple the liquid receiving region to an aerosol generator. In this way, liquid from the liquid receiving region is permitted to flow to the aerosol generator for aerosolization.

In one aspect, the liquid receiving region includes an overflow region that extends along side the ampoule region above the bottom end of the ampoule. In this way, excess liquid from the ampoule may overflow into the overflow region until reaching the same height as the liquid within the ampoule. Such a configuration is useful in reducing the overall size of the aerosol generator since the overflow region may be along side the ampoule.

In another aspect, the liquid receiving region includes a tapered bottom end with a drain opening to funnel liquid from the ampoule to the aerosol generator. With such a configuration, the interface may be used to produce a seal between the bottom end of the liquid receiving region and the aerosol generator. Such a seal may be formed, for example, by coupling a seal member to the bottom end of the liquid receiving region, to the aerosol generator or both. In some cases, the aerosol generator may also include an interface to produce a sealed pathway between the bottom end of the liquid receiving region.

In one particular aspect, the feed system housing includes a top portion and a bottom portion having the tapered bottom end. The top portion is attachable to the bottom portion to permit the top portion to be used as a disposable unit. For example, the bottom portion may be a component of an aerosolization device and the top portion may be marketed as a disposable unit containing the ampoule. In this way, the top portion having the ampoule may be inserted into the aerosolization device and coupled with the bottom portion. The liquid may then be released from the ampoule and permitted to flow into the bottom portion. With such an embodiment, the ampoule region and the overflow region may comprise two elongate channels extending through the top portion so that overflow liquid may rise into the overflow region as previously described. Conveniently, an o-ring seal may be positioned between the top portion and the bottom portion to provide an appropriate seal.

In some cases, the feed system may include a lid that is coupled to the housing to secure the ampoule within the ampoule region. When the ampoule includes a top tab extending from the top end, and the lid may include a slot through which the top tab extends. The lid prevents the ampoule from being removed from the top portion of the feed system so that the entire unit may be disposable. After insertion into the aerosolization device, the top tab may be removed to form a vent opening in the top end of the ampoule.

The ampoule may also include a bottom tab extending from the bottom end. This bottom tab may also be removable to form a drain opening in the bottom end of the ampoule, preferably before insertion into the aerosolization device and prior to forming the vent. In cases where the ampoule is secured within the top portion of the feed system, the bottom tab extends distally beyond the top portion of the housing. With such a configuration, the bottom tab is removed prior to insertion of the top portion into the aerosolization device. The top tab may then be removed to vent the liquid into the liquid receiving region. Further, it will be appreciated that other opening schemes may be used, such as by using cracking tabs and/or including piercing elements within the feed system that pierce the ampoule upon insertion and/or closing of a lid.

In some embodiments, the feed system may be configured to be integrally formed with an aerosolization device so that the liquid feed system may be continuously reused along with the device. With such embodiments, a user simply places an ampoule into the device and then releases the liquid from the ampoule where the liquid flows into the liquid receiving region and is available for aerosolization. Once aerosolization is finished, the ampoule is removed and discarded. Another ampoule may then be inserted and the process repeated. In some cases, the entire feed system may be removably held within the aerosolization device so that it may be removed for cleaning. Further, other components, such as the aerosol generator and an inhalation sensor may be coupled to the liquid feed system so that they may be removed along with the feed system during cleaning.

In another aspect, the aerosol generator may comprise a vibratable member having a plurality of apertures and a vibratable element to vibrate the vibratable member. For example, the aerosol generator may have an aperture plate with tapered apertures, and a piezo electric element may be used to vibrate the aperture plate.

The invention further provides an exemplary method for aerosolizing a liquid. According to the method, an ampoule containing a liquid is inserted into an aerosolization device having a liquid feed system, an aerosol generator, and an exit opening. The ampoule is opened to permit liquid from the ampoule to drain into a liquid receiving region of the feed system. The aerosol generator is then operated to eject liquid droplets through the exit opening.

In one aspect, a bottom tab is removed from the ampoule to form a drain opening before inserting the ampoule into the aerosolization device. Once in the device, a top tab may be removed to form a vent opening in the ampoule. In another aspect, the ampoule is held within a receiver unit of the liquid feed system. With this configuration, the receiver unit is inserted into the aerosolization device after removal of the bottom tab and coupled with the liquid receiving region. In this way, the receiver unit may be packaged as a disposable unit having an ampoule.

Alternatively, the feed system may include one or more piercing elements that pierce the ampoule during insertion and/or closing of a lid. In another aspect, the receiver unit includes an overflow region adjacent to the ampoule. When the ampoule is opened excess liquid flows into the overflow region until aerosolized. In a further aspect, an aperture plate of the aerosol generator is vibrated to produce the liquid droplets.

DESCRIPTION OF THE SPECIFIC EMBODIMENTS

Figure 1:
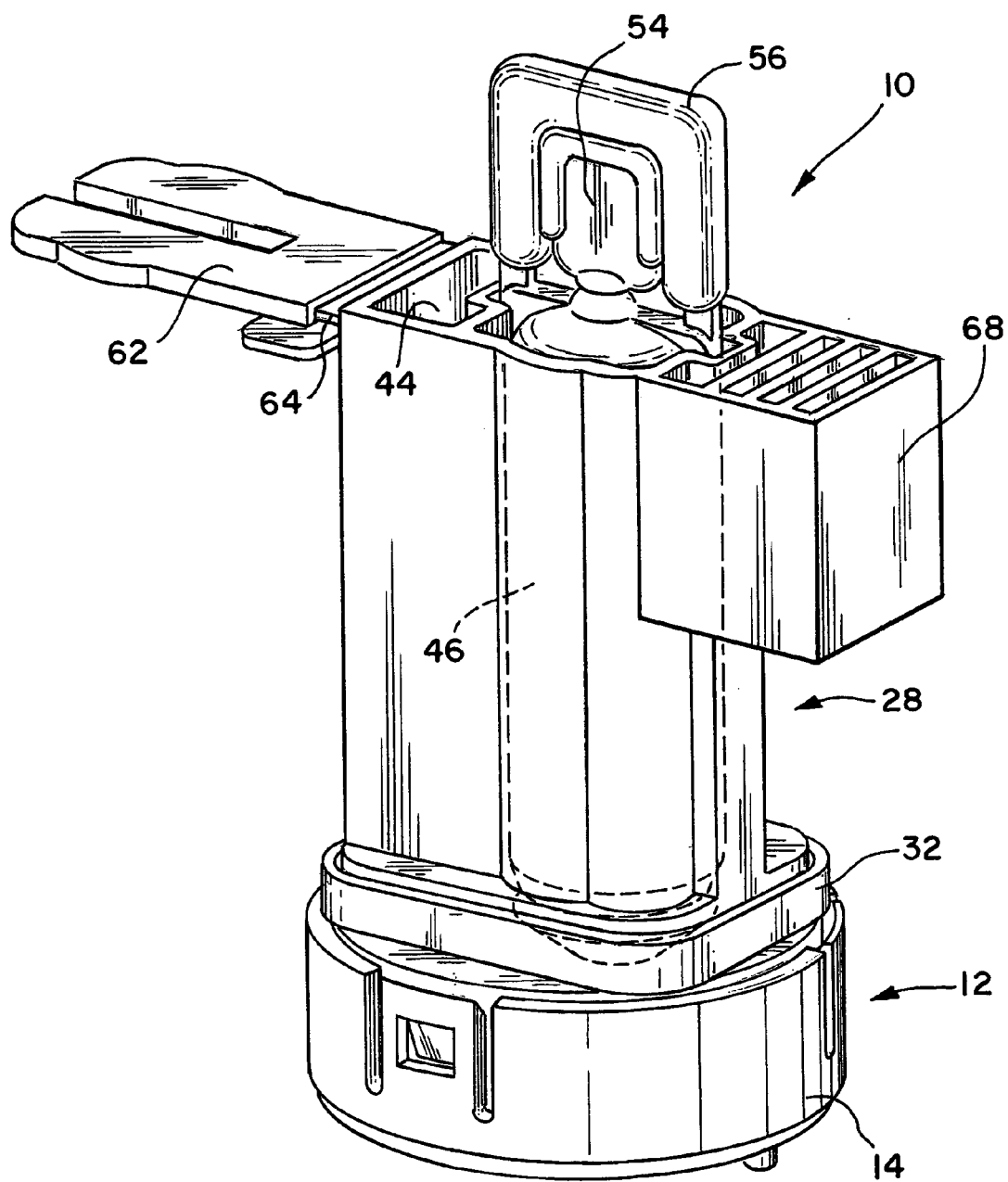
FIG. 1 is a top perspective view of a liquid feed system coupled to an aerosol generator according to the invention.

The invention provides various liquid feed systems for aerosolization devices along with methods for their use. The liquid feed systems may be used with a variety of aerosolization devices that are configured to aerosolize a volume of liquid. Such aerosolizers may be of the type, for example, where a vibratable member is vibrated at ultrasonic frequencies to produce liquid droplets. Some specific, non-limiting examples of technology for producing fine liquid droplets is by supplying liquid to an aperture plate having a plurality of tapered apertures and vibrating the aperture plate to eject liquid droplets through the apertures. Such a technique is described generally in U.S. Pat. Nos. 5,164,740; 5,938,117; 5,586,550; 5,758,637 and 6,085,740, the complete disclosures of which are herein incorporated by reference. However it will be appreciated that the invention is not intended to be limited for use with only such devices.

The feed systems of the invention utilize a container that holds a liquid, such as an ampoule, vial, or other means of holding fluid in a closed space. Such containers are typically sealed and must be processed to release the liquid. The containers may be processed by removing or operating one or more tabs, by piercing the containers, or the like. Merely by way of example, some ampoules that may be used with the invention are described in copending U.S. patent application Ser. No. 09/8 12,755, filed Mar. 20, 2001, published as U.S. Patent Application Publication No. 2002/0134377 on Sep. 26, 2002, the complete disclosure of which is herein incorporated by reference.

The feed systems further include a liquid receiving region that defines a path or shape of a secondary volume area that transfers the liquid from the initial container or ampoule to the aerosol generator. The feed systems may also include an interface with the aerosol generator. One feature of such feed systems is that they may be constructed of similar components that permit the feed system to be loadable as an entire disposable system into an aerosolization device, or to be integrated into an aerosolization device where the ampoule is inserted directly into the aerosolization device. Such convertibility may be accomplished using a majority of the same parts, with the manufacturer choosing how the aerosolization device is configured to fit the user's drug type, aerosol parameters, frequency of use, and the like.

The liquid receiving region may be oriented entirely below the ampoule to facilitate the gravity drainage of a percentage of the ampoule when starting the aerosolization process. This can be either a small percentage of ampoule drainage, and thus a small volume of space, a large percentage of ampoule drainage and an associated larger volume of space, or anywhere in between full initial drainage and minimal initial drainage of the ampoule volume. The amount of vertical space available in the aerosolization device, as well as the volume of liquid contained within the ampoule can dictate the size of the liquid receiving region. The interface of the feed system may be configured in a variety of ways to appropriately interface the liquid receiving region to the aerosol generator. For example, the interface may comprise an adhesive bond between the liquid receiving region and the aerosol generator. As another example, the interface may be compression sealed to the aerosol generator, or the interface may be held in place with a tight tolerance, actually touching the aerosol generator, but not damping it. An objective of such techniques is to connect a pathway between the liquid receiving region and the aerosol generator, in effect sealing off the fluid path from the environment. Such an interface is provided without significantly dampening the vibration of the piezoelectric crystal adhered to the aerosol generator in such a way as to impede the aerosolization flow rate.

The path or shape of the liquid receiving region may be oriented partially below and partially beside the ampoule to facilitate a reduction in the amount of vertical space taken up by the liquid receiving region, as well as to facilitate the venting of air from the liquid receiving region. The amount of volume in either the space below or the space beside the ampoule may be dictated by the requirements of the aerosolization device, and the rate and ease of which the liquid will drain out of the ampoule. The amount of space above and below the ampoule, may be either a small percentage of ampoule drainage, and thus a small volume of space, a large percentage of ampoule drainage and an associated larger volume of space, or anywhere in between full initial drainage or minimal initial drainage of the ampoule volume. The amount of vertical space available in the aerosolization device, as well as the volume of liquid contained within the ampoule may also dictate the size of the liquid receiving region.

One feature of the invention is that the feed system may be a unit that is separate from an aerosolization device. In this way, the feed system may be removed from the aerosolization device following aerosolization and disposed, while the aerosolization device may be reused simply by inserting another feed system unit. With such an embodiment, the ampoule is positioned and sealed into the feed system unit during manufacturing, so that the user cannot tamper with the position or contents of the ampoule until the aerosolization device is activated for use. With such a configuration, the aerosolization device may be actuated in at least two ways. If using an ampoule having twist off tabs, the user may twist off a drain orifice tab, and insert the feed system unit into the aerosolization device. The insertion of the feed system unit into the aerosolization device seats the feed system unit against a sealing material, of a generally softer durometer, or a precision harder durometer material, and seals the fluid path from the ampoule to the aerosol generator. Once the user has the tactile feedback that the feed system has been seated and sealed in the aerosolization device, e.g. by a perceptible click, the top vent tab may be twisted off, allowing the free flow of fluid from the ampoule into the liquid receiving region. From the liquid receiving region, the liquid flows to the aperture plate of the aerosol generator.

If the ampoule includes a bottom twist off tab and a top cracking tab, after twisting off the bottom tab and seating the feed system unit in the aerosolization device, the user may close a lid of the aerosolization device. In so doing, the top tab is bent, cracking the air seal and venting the contents of the ampoule so that the liquid may flow into the liquid receiving region and into the path of the aerosol generator.

If using a pierce ampoule in the disposable configuration, the user may simply load the feed system unit into the aerosolization device, and close the lid. In so doing, pins located in the feed system unit pierce both a top air vent and a bottom drain nipple, allowing fluid to flow into the liquid receiving region, and into the path of the aerosol generator.

In some embodiments, the feed system may be an integral or a permanent portion of the device aerosolization device. The feed system may be positioned and sealed into the aerosolization device without an ampoule during manufacture. For example the feed system may be adhesive bonded or snap fitted into the aerosolization device during manufacture. In such a case, the user is instructed to insert the ampoule into the feed system when ready to aerosolize a liquid. The option of snap or latch fitting of the feed system into place in the aerosolization device is desirable for occasionally removing the feed system for cleaning. With both the dispersible and reusable embodiments, most of the components may be interchangeable. In this way, the same manufacturing process may be used to make parts for both embodiments.

Such an aerosolization device may be actuated by at least two methods. If using a twist off ampoule, the user twists off a drain orifice tab, and inserts the ampoule into the feed system. The insertion of the ampoule into the feed system seats the ampoule against either a firm material, allowing the ampoule to conform to the seal area, or against a softer material which provides most of the sealing compliance, and seals the ampoule into the device. In one aspect, a seal is formed between the outer diameter of the ampoule and the inner diameter of the liquid feed system. Alternatively, a seal may be provided between the inner diameter of the ampoule and the outer diameter of a receptacle portion of the feed system. Once the user has the tactile feedback that the ampoule has been seated and sealed in the aerosolization device, e.g. by a perceptible click, the top vent tab may be twisted off, allowing the free flow of fluid from the ampoule into the liquid receiving region. If the ampoule is a bottom twist off, top cracking ampoule, after twisting off the bottom tab of the ampoule and seating the ampoule in the device, the user may close the lid of the device to bend the top tab. Bending of the top tab cracks the air seal and vents the contents of the ampoule into the liquid receiving region and into the path of the aerosol generator.

If using a pierce ampoule with the aerosolization device that already includes a feed system, the user simply loads the ampoule into the aerosolization device. Upon closing the lid, a pin in a bottom of the feed system and another pin located in a lid or top of the feed system pierce both a top air vent and a bottom drain nipple. This allows fluid to flow into the liquid receiving region, and into the path of the aerosol generator.

The feed systems of the invention may be constructed to include other disposable components of an aerosolization device, such as a breath trigger switch, an aerosol generator, or both. This allows for easy packaging and user convenience, as well as a means of ensuring that the user obtains only one cycle from the combined components. When the feed system is incorporated into the aerosolization device at the time of manufacture, the combination of components makes assembly simple, and allows the user a one step operation for swapping out replacement parts. There is also an advantage to combining components in such an embodiment for the purposes of routine cleaning and inspection of the such parts or components.

The feed systems of the invention are also compatible with either a face seal interface, or a frame seal interface to the aerosol generator. The face seal configuration allows the feed system to be directly attached to the aerosol generator, and is useful when the feed system is removable. The face seal may be attached to the feed system or to the aerosol generator. Attachment of the seal to the feed system ensures seal replacement whenever the feed system is replaced. The frame seal configuration allows the feed system to attach to a permanent part of the device, such as the housing defining the liquid receiving region or a frame which holds the aerosol generator in place.

Figure 2:
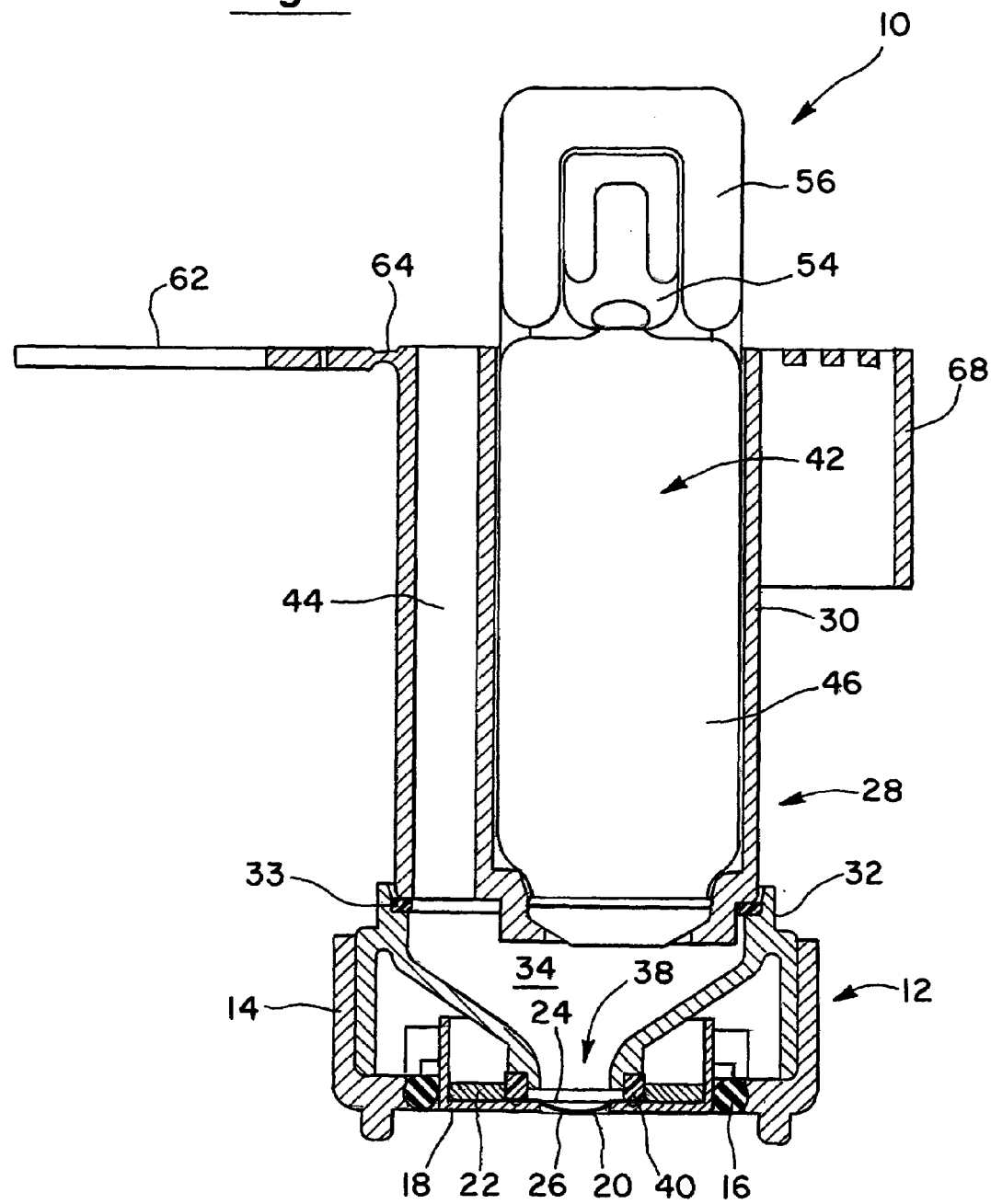
FIG. 2 is a cross sectional view of the liquid feed system and aerosol generator of FIG. 1.
Figure 3:
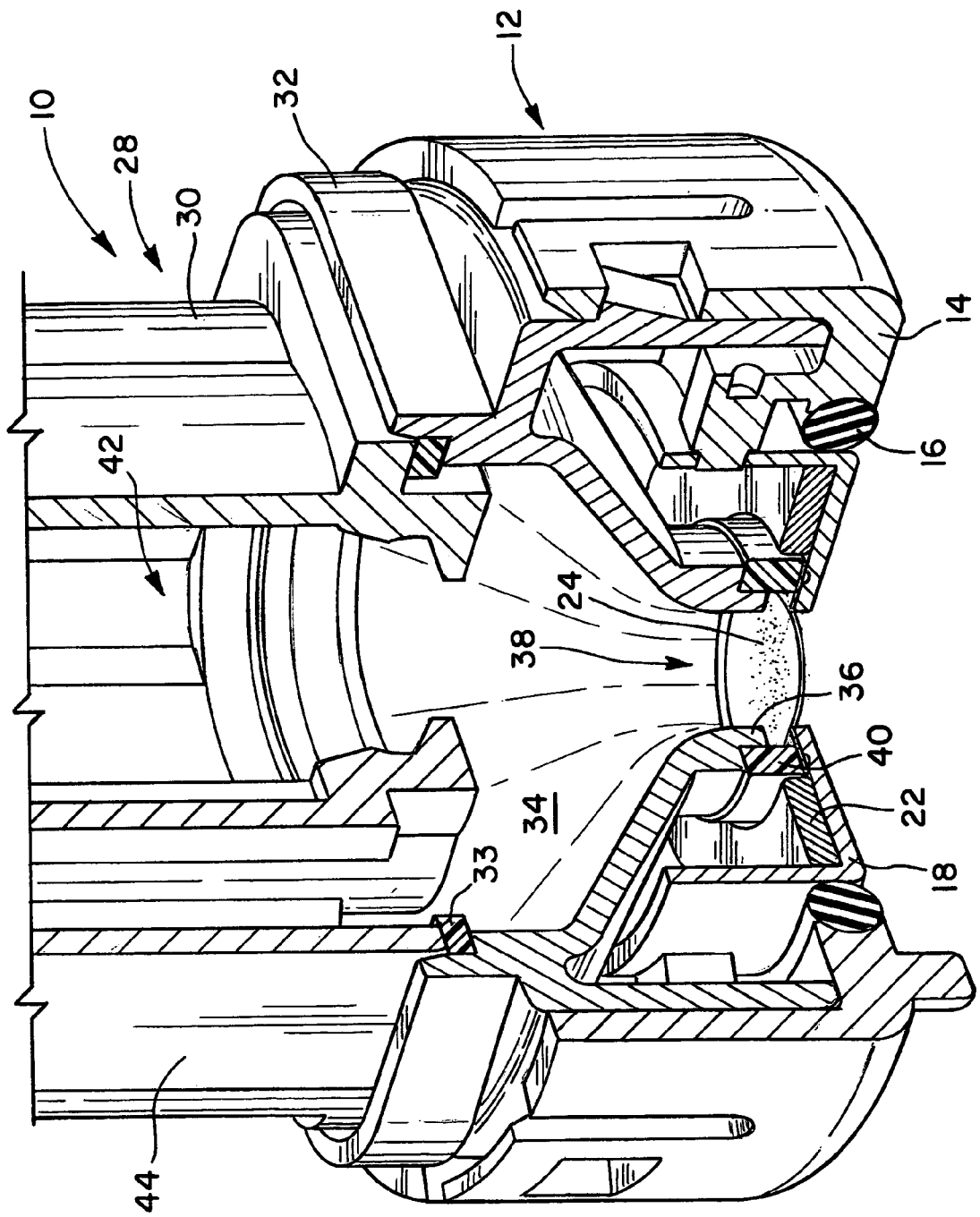
FIG. 3 is a cut away view of the liquid feed system and aerosol generator of FIG. 1 shown without an ampoule.
Figure 4A:
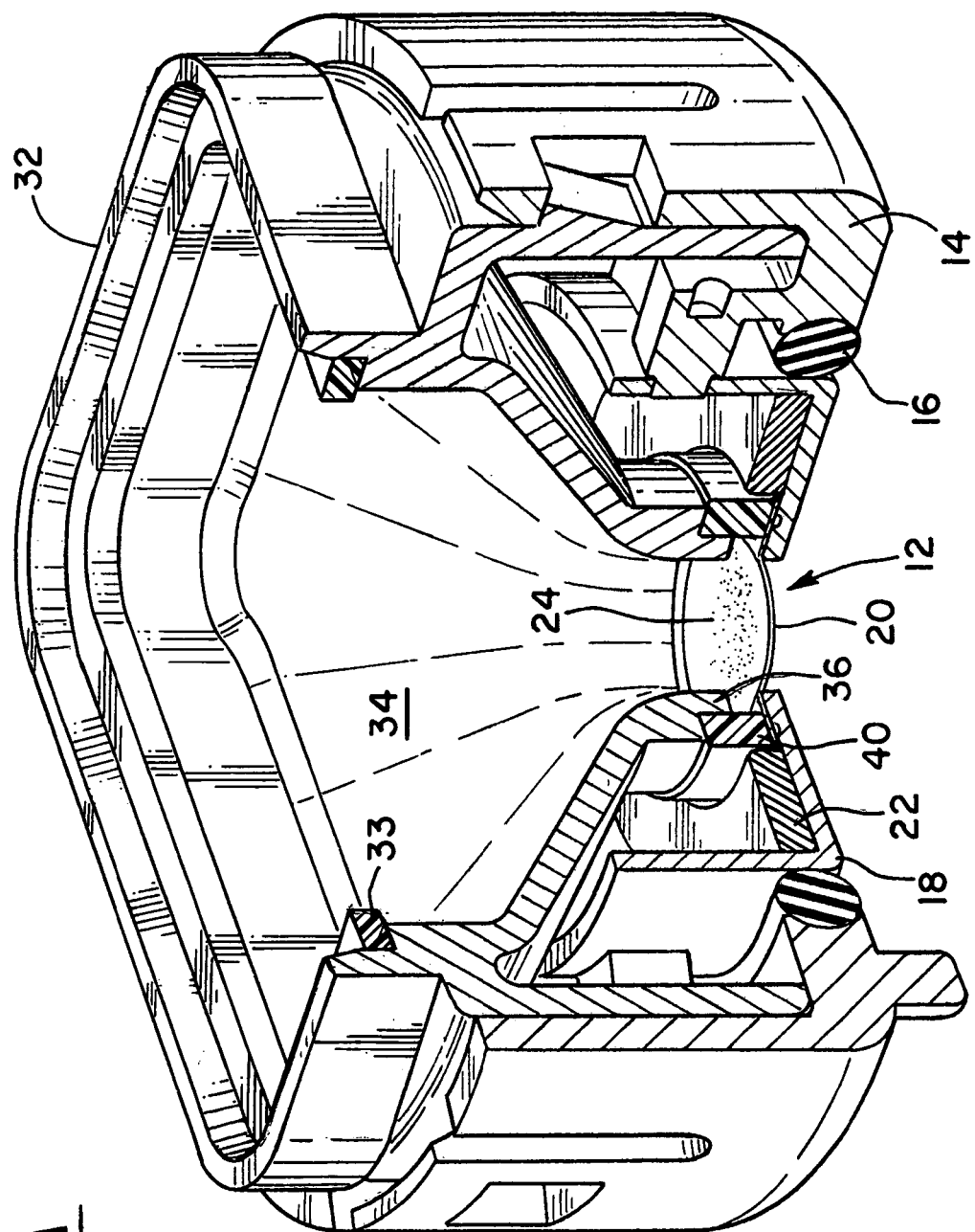
FIG. 4A is a cut away view of a bottom portion of the liquid feed system of FIG. 3 when coupled to the aerosol generator.
Figure 4B:
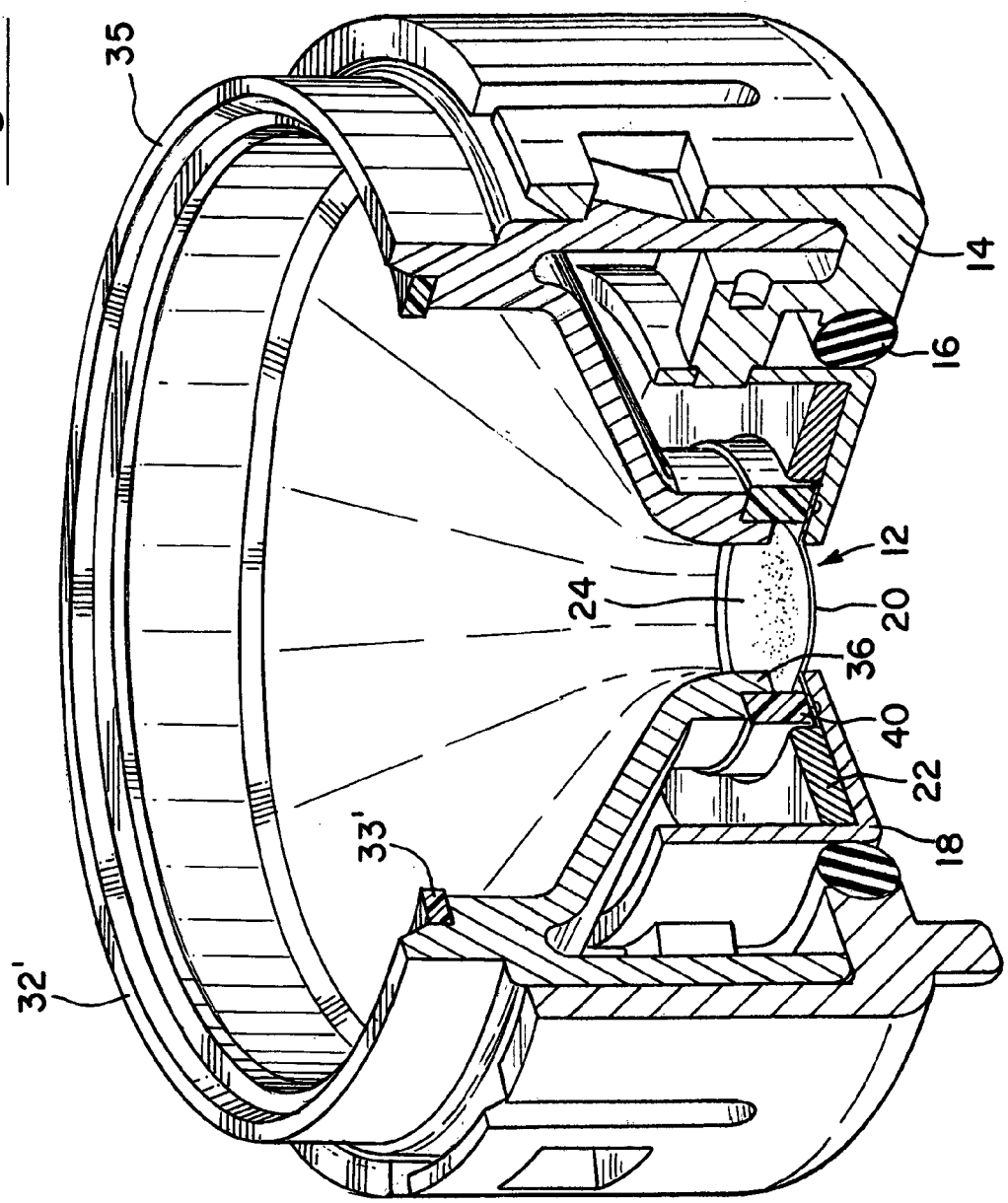
FIG. 4B is a cut away view of an alternative bottom portion of a liquid feed system according to the invention.
Figure 5:
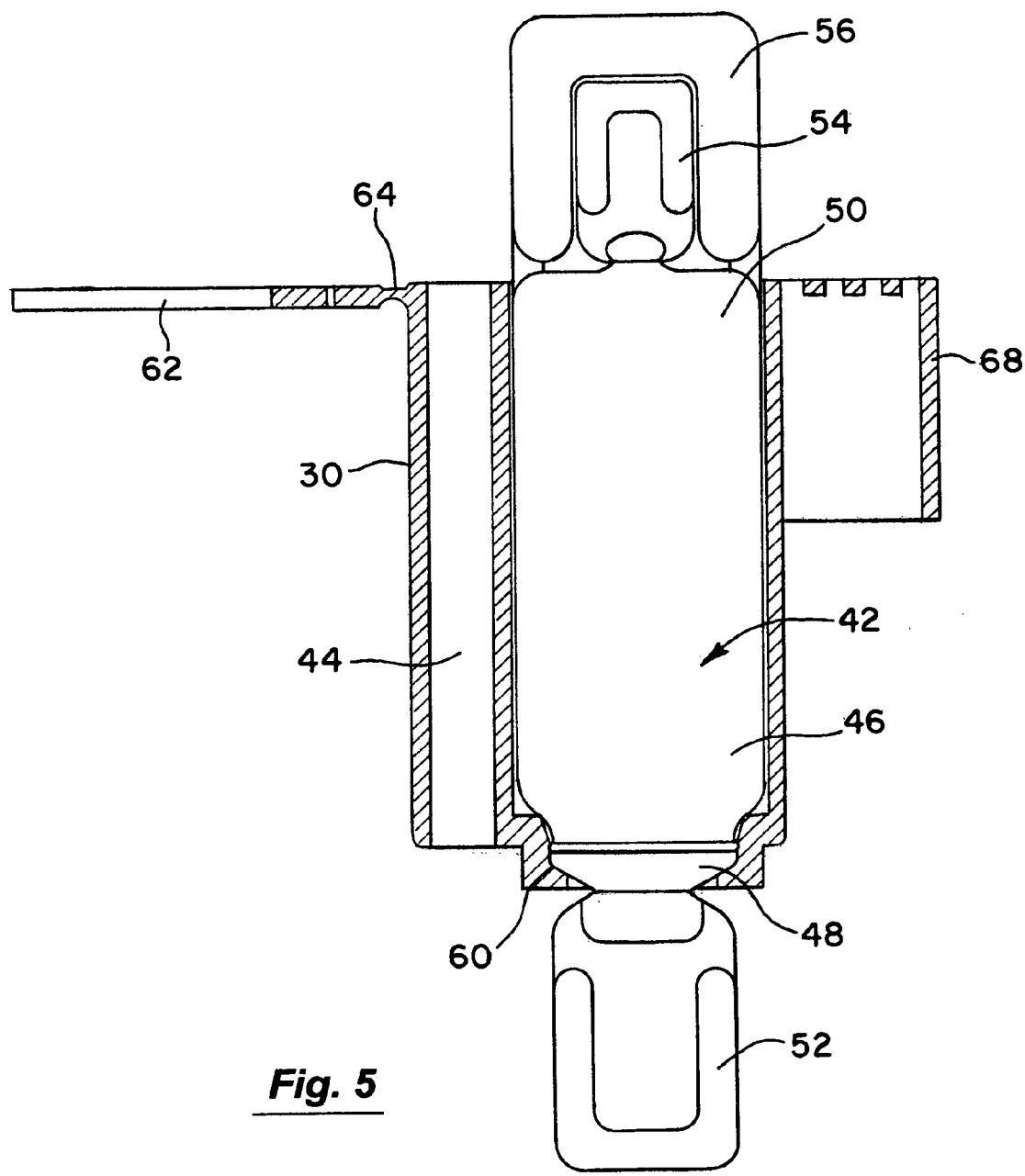
FIG. 5 is a cross sectional view of a top portion of the liquid feed system of FIG. 1.
Figure 6:
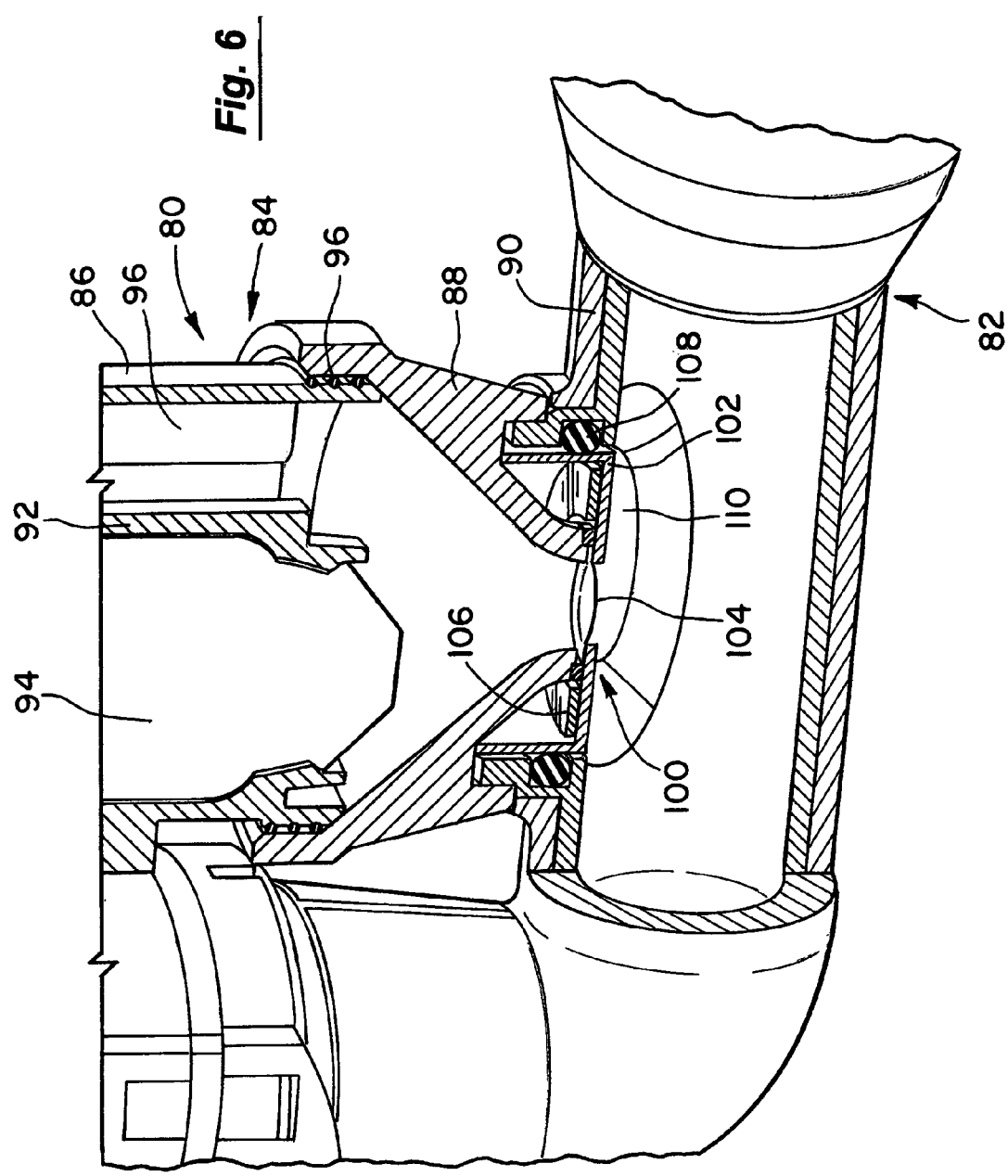
FIG. 6 is a cross sectional view of an alternative liquid feed system having ring seals that seal a top portion to a bottom portion of the feed system according to the invention.

Referring now to FIGS. 1–3, one embodiment of a liquid feed system 10 will be described. To illustrate how feed system interacts with an aerosolization device, feed system 10 is shown coupled to an aerosol generator 12. However, it will be appreciated that feed system 10 may be used with a variety of aerosol generators, and the invention is not limited to the particular aerosol generator shown. Aerosol generator 12 may be constructed in a manner similar to the aerosol generators described in U.S. Pat. Nos. 5,164,740; 5,938,117; 5,586,550; 5,758,637 and 6,085,740, previously incorporated by reference. Aerosol generator 12 includes a frame 14 that is used to couple aerosol generator 12 to another structure of the aerosolization device, such as to a device housing. Coupled to frame 14 by an o-ring 16 is a cup shaped support member 18 to which is coupled a vibratable member 20 having a plurality of apertures. Also coupled to support member 18 is an annular piezo electric member 22 that is used to vibrate vibratable member 20. In operation, liquid is supplied to a rear surface 24 of vibratable member 20, and liquid is ejected from a front surface 26 upon vibration of vibratable member 20.

Feed system 10 is constructed of a feed system housing 28 having a top portion 30 and a bottom portion 32. As shown, top portion 30 is separate from bottom portion 32, and a seal 33 is used to create a fluid tight seal between the two portions. However, it will be appreciated that in some embodiments, the two portions may be integrally formed together. Bottom portion 32 defines a liquid receiving region 34 and is coupled to aerosol generator 12. More specifically, bottom portion 32 includes a taped bottom end 36 that leads to an opening 38 just above rear surface 24 of vibratable member 20. In this way, liquid within bottom portion 32 flows by assistance of gravity onto rear surface 24 where it may be aerosolized. Hence, bottom end 36 serves as an interface with aerosol generator 10. At bottom end 36 is a seal 40 that provides a fluid tight seal between bottom portion 32 and aerosol generator 10. Seal 40 may be constructed of a resilient material and may be compression sealed to aerosol generator 10 or held in place with a tight tolerance to minimize damping of vibratable member 20. Seal 40 may conveniently be attached to bottom end 36 or to support member 18.

Top portion 30 includes an ampoule region 42 and a liquid overflow region 44. Held within ampoule region 42 is an ampoule 46 having a bottom end 48 and a top end 50. Ampoule 46 may be similar to the ampoule described in copending U.S. application Ser. No. 09/812,755, filed Mar. 20, 2001, published as U.S. Patent Application Publication No. 2002/0134377 on Sep. 26, 2002, previously incorporated herein by reference. Ampoule 46 includes a twist of bottom tab 52 (see FIG. 5) and a twist off top tab 54 that is surrounded by a bendable shroud 56. In FIGS. 1–3, bottom tab 52 has been removed to form a drain opening prior to insertion into feed system 10. When ready to release the liquid from ampoule 46, shroud 58 is bent and top tab 56 is twisted off to form a vent. Liquid within ampoule 46 then drains into liquid receiving region 34, with any overflow rising into overflow region 44 until reaching the height of the liquid within ampoule 46. As the liquid is aerosolized, the liquid in overflow region 44 and within ampoule 46 drains at the same rate. In this way, feed system 10 may be constructed with a relatively narrow geometry to reduce the overall size of the aerosolization device. However, it will be appreciated that liquid receiving region 34 may be made large enough so that overflow region 44 is not needed. Further, although shown with ampoule 46, it will be appreciated that other types of ampoules may be used that are opened in different ways.

Ampoule region 42 may conveniently be constructed to have a shape that matches the shape of ampoule 46. Further, ampoule 46 has an outer perimeter 60 that contacts top portion 30 to form a fluid tight seal between ampoule 46 and top portion 30. Top portion 30 may further include a ridge which top portion 30 passes over to give the user tactile feedback indicating ampoule 46 has been properly inserted. Use of outer perimeter 60 is further advantageous in that it provides a relatively large sealing area on top portion 30 to facilitate cleaning once ampoule 46 has been removed (see FIG. 3).

Feed system 10 may further include a lid 62 that is attached to top portion 30 by a hinge 64. Lid 62 further includes a slot 66 that permits lid to close over shroud 58 and top tab 56. In this way, once lid 62 is closed, ampoule 46 is secured within feed system 10. Use of lid 62 is particularly advantageous when top portion 30 is used as an insertable unit into an aerosolization device. By using lid 62, ampoule 46 may be secured within top portion 30 at the time of manufacture and then sold as a disposable unit as described hereinafter.

Feed system 10 may optionally include a flow sensor 68 that senses when a user inhales from an aerosolization device. When an inhalation is sensed, a signal may be sent to a controller in the aerosolization device to actuate piezo electric member 22. Flow sensor 68 may be similar to any of the flow sensors described in U.S. Pat. No. 6,014,970 and copending U.S. patent application Ser. No. 09/705,063, filed Nov. 2, 2000, the complete disclosures of which are herein incorporated by reference. By including flow sensor 68 on top portion 30, the flow sensor may also be configured as a disposable unit after the liquid is aerosolized and top portion 30 is removed.

As shown in FIGS. 4A and 5, top portion 30 is removable from bottom portion 32. In this way, bottom portion 32 may be incorporated into an aerosolization device (where it is coupled to aerosol generator 12 as shown in FIG. 4A), while top portion 30 is a separate unit that is insertable into the aerosolization device. In this way, a specific type of ampoule may be included within top portion 30 at the time of manufacture, and top portion 30 sold as a disposable unit. With such a configuration, ampoule 46 includes both top tab 56 and bottom tab 54 when held within top portion 30 as shown in FIG. 5. When ready for use, bottom tab 54 is removed to form the drain opening. Top portion 30 is then inserted into the aerosolization device unit top portion 30 couples with bottom portion 32. These two portions may be configured to snap together or give some other type of tactile feedback to let the user know when top portion 30 has been properly inserted. Shroud 58 is then bent and top tab 56 removed to provide a vent opening. The liquid within ampoule 46 then drains into bottom portion 32 where it may be aerosolized. Following aerosolization, top portion 30 may be removed from the aerosolization device and discarded. Another top portion with a fresh ampoule may then be inserted and the process repeated.

Alternatively, feed system housing 28 may be constructed as a single part (or of the same parts that are secured together) so that the entire feed system may part of the aerosolization device. In this way, ampoules may be inserted and removed when needed. In some cases, the entire feed system 10 may be removable from the aerosolization device (with or without the aerosol generator 10). For example, feed system 10 (with or without the aerosol generator) could be snap fit into place within the aerosolization device. Alternatively, some other type of tactile feedback may be provided to indicate that the feed system has been properly inserted. Use of a removable feed system permits the feed system to be removed for cleaning of both the device and the feed system. Once cleaned, the feed system may simply be inserted back into the aerosolization device.

Bottom portion 32 may be modified to include a variety of connectors that removably connect bottom portion 32 to top portion 30. For example, as shown in FIG. 4B a bottom portion 32' include a circular flange 35 to mate with a corresponding circular flange on the top portion. Further, a circular seal 33' is used to provide a fluid tight seal between the top portions. All other elements may be configured to be essentially the same as in bottom portion 32. Although shown as circular, it will be appreciated that a variety of other shapes and other types of connection schemes may be used to couple the two halves together.

FIG. 6 illustrates an alternative embodiment of a feed system 80 that is held within an aerosolization device 82. Feed system 80 comprises a housing 84 having a top portion 86 and a bottom portion 88. Feed system 80 is constructed so that bottom portion 88 remains within device 82 during multiple uses, while top portion 86 is a disposable unit. As such, bottom portion 88 is coupled to a frame 90 of device 82. Conveniently, bottom portion 88 may be removably attached to frame 90, e.g., by a snap fit, or may be integrally molded as part of frame 90. Similar to other embodiments, top portion 86 includes a ampoule region 92 that includes an ampoule 94, and an overflow region 96. Ampoule 94 may be inserted into ampoule region 92 at the time of manufacture to permit top portion 86 to be inserted into device 82 as a unit.

Top portion 86 further includes a set of piston ring seals 98 that form a fluid tight seal between top portion 86 and bottom portion 88 when connected. In this way, liquid from ampoule 94 that flows into overflow region 96 will not leak out of feed system 80. Such a seal may also be used with the other embodiments described herein.

Device 82 further includes an aerosol generator 100 that comprises a support member 102 that holds a vibratable member 104 having a set of tapered apertures. Also coupled to support member 102 is a piezo electric member 106 that is actuated to vibrate vibratable member 104. An o-ring seal 108 is positioned between support member 102 and frame 90. Bottom member 88 is interfaced to support member 102 by an adhesive bond so that liquid from the ampoule does not leak through this interface. Vibratable member 104 is positioned near an exit opening 110, such as an exit opening of a mouthpiece, so that aerosolized liquids may exit device 82.

In use, top portion 86 is inserted into device 82 after a bottom tab has been removed from the bottom of ampoule 94 in a manner similar to that described with other embodiments. Top portion 86 is firmly seated into bottom portion 88 until a fluid tight seal is formed. The top tab on ampoule 94 may then be removed to permit the liquid within ampoule 94 to drain into bottom portion 88, with any overflow rising into overflow region 96. Aerosol generator 100 is actuated to aerosolize the liquid where it may be withdrawn from device 82 through exit opening 110. After aerosolization, top portion 86 is removed from device 82 and discarded. Another top portion with a fresh ampoule may then be inserted and the process repeated.

Figure 7:
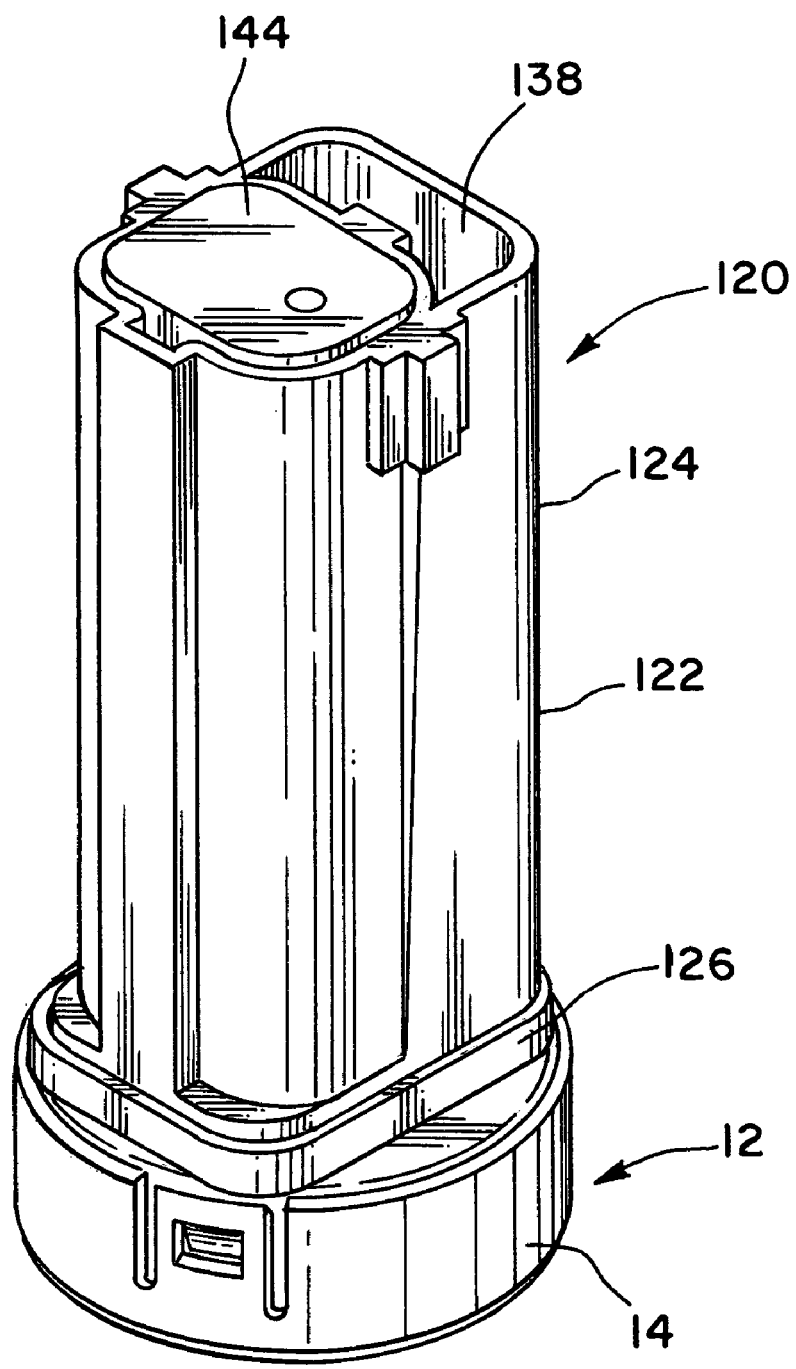
FIG. 7 is a top perspective view of another embodiment of a liquid feed system coupled to an aerosol generator according to the invention.
Figure 8:
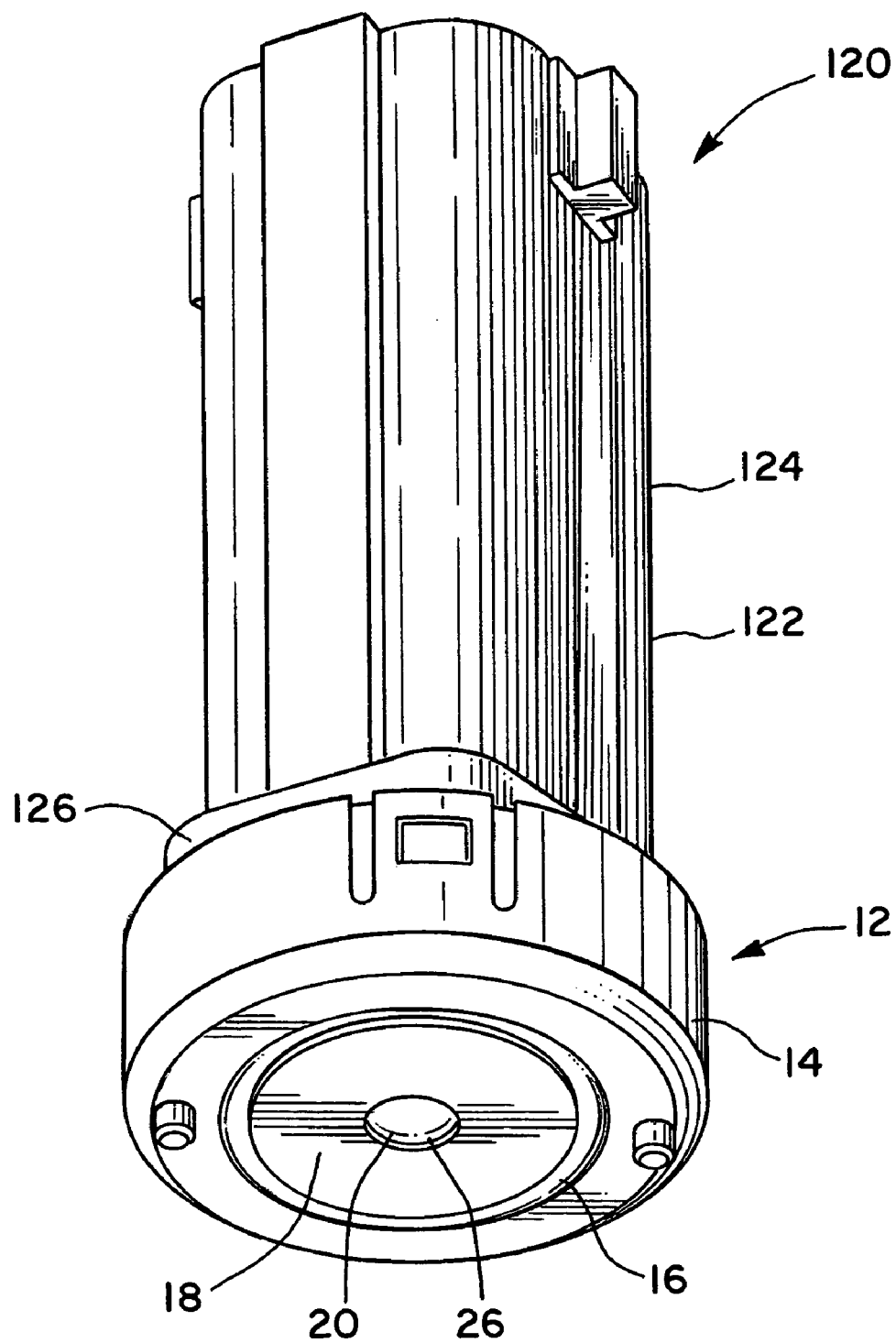
FIG. 8 is a bottom perspective view of the liquid feed system and aerosol generator of FIG. 7.
Figure 9:
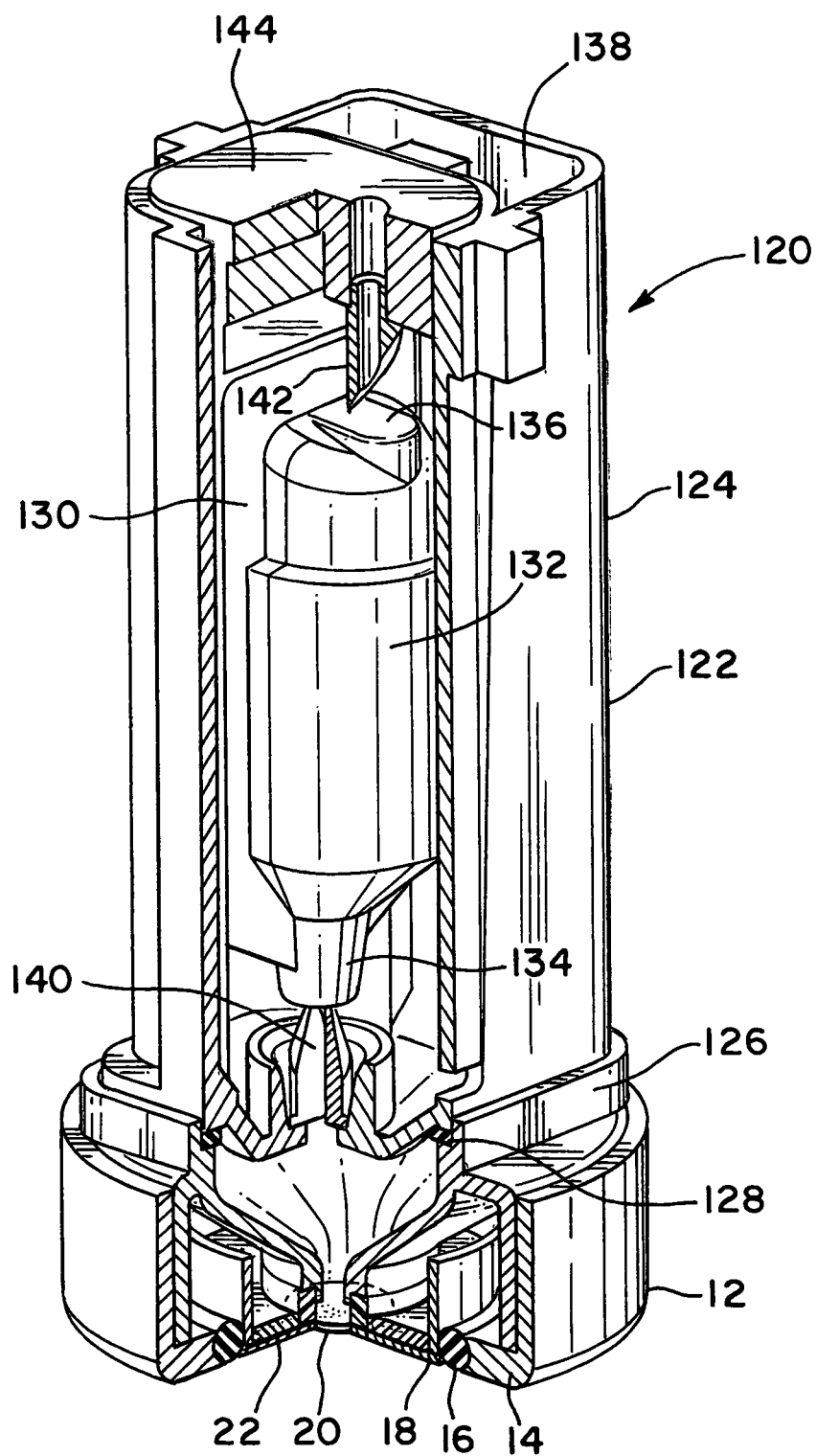
FIG. 9 is a cut away view of the liquid feed system and aerosol generator of FIG. 7.

FIGS. 7–9 illustrate another embodiment of a feed system 120. Feed system 120 comprises a feed system housing 122 having a top portion 124 and a bottom portion 126. Similar to other embodiments, these two portions may be formed as an integral unit or separate and may be either integrally formed with or removably attached to an aerosolization device. Further, top portion may be a disposable unit containing an ampoule, or may be configured to reusable and receive a new ampoule during each use. As shown, a seal 128 is positioned between top portion 124 and bottom portion 126 to provide a fluid tight seal. In this way, top portion 124 may be a removable unit that may be disposed of after each use. Alternatively, seal 128 may be used even when top portion 124 is not intended to be a disposable unit so that a single set of parts may be manufactured for multiple types of aerosolization device configurations similar to other embodiments.

Top potion 124 includes an ampoule region 130 containing an ampoule 132 having a bottom end 134 and a top end 136, and an overflow region 138. Ampoule 132 is configured to be opened by piercing bottom end 134 and top end 136 rather than by using twist off tabs. However, it will be appreciated that a twist of tab could be used on bottom end 134 or top end 136 in combination with an end that is pierced. As shown, top portion 124 further includes a bottom piercer 140 that is positioned below bottom end 134 and a top piercer 142 that is coupled to a depressible lid 144. In this way, liquid may be removed from ampoule 132 by depressing lid 144 into ampoule region 130 until bottom end 134 is pierced by bottom piercer 140 and top end 136 is pierced by piercer 142. When opened, liquid flows from bottom end 134 and into bottom portion 126, with any overflow rising into overflow region 138.

Bottom portion 126 is coupled to an aerosol generator that is used to aerosol the liquid. As shown, the aerosol generator is essentially identical to aerosol generator 12 and, for convenience of discussion, will be referred to with the same reference numerals. Frame 14 may be an integral part of an aerosolization device, or may be a snap in part that permits the entire feed system to be removed, such as during cleaning. In this way, the same parts may be used for both integrated and removable feed systems, as well as with integrated and removable top portions 124 as previously described.

After the liquid has been dispensed from ampoule 132, lid 144 may be removed and another ampoule inserted. Alternatively, top portion 124 may be removed, disposed, and replaced with another top portion with a fresh ampoule.

The invention has now been described in detail for purposes of clarity and understanding. However, it will be appreciated that certain change and modifications may be practiced within the scope of the appended claims.

What is claimed is:

1. A feed system for an aerosolizer, the aerosolizer having a feed system comprising:
    a feed system housing having a first region that is adapted to receive container that holds a liquid, and that includes a bottom end and a top end, the feed system housing having a liquid receiving region that is adapted to receive liquid dispensed from the container, wherein the liquid receiving region includes an overflow region that extends along side the first region above the bottom end of the container; and
    an interface that is adapted to couple the liquid receiving region to an aerosol generator, whereby liquid from the liquid receiving region is permitted to flow to the aerosol generator for aerosolization.

2. A feed system as in claim 1, wherein the liquid receiving region includes a tapered bottom end with a drain opening to funnel liquid from the container to the aerosol generator.

3. A feed system as in claim 2, wherein the interface is adapted to produce a seal between the bottom end of the liquid receiving region and the aerosol generator.

4. A feed system as in claim 2, wherein the feed system housing includes a top portion and a bottom portion having the tapered bottom end, wherein the top portion is attachable to the bottom portion, and wherein the first region and the overflow region each comprise an elongate channel extending through the top portion.

5. A feed system as in claim 4, further comprising an o-ring seal positioned between the top portion and the bottom portion.

6. A feed system as in claim 1, farther comprising a lid coupled to the feed system housing that is adapted to secure the container within the first region.

7. A feed system as in claim 6, wherein the lid includes a slot that is adapted to receive a top tab that extends from the top end of the container.

8. An aerosolization device, comprising:
    an aerosolization device housing having an interior and an exit opening;
    an aerosol generator disposed within the device housing to eject an aerosolized liquid through the exit opening, wherein the aerosol generator comprises a vibratable member having a plurality of apertures and a vibratable element to vibrate the vibratable member;
    a liquid feed system disposed within the device housing, the liquid feed system comprising a feed system housing having a first region that is adapted to receive a container that holds a liquid, a liquid receiving region that is adapted to receive liquid dispensed from the container, and an interface that couples the liquid receiving region to the aerosol generator, whereby liquid from the liquid receiving region is permitted to flow to the aerosol generator for aerosolization.

9. A device as in claim 8, wherein the container includes a top end and a bottom end, and the liquid receiving region includes an overflow region that extends along side the first region above the bottom end of the container.

10. A device as in claim 8, wherein the liquid receiving region includes a tapered bottom end with a drain opening to funnel liquid from the container to the aerosol generator.

11. A device as in claim 10, wherein the interface includes a seal member to produce a seal between the bottom end of the liquid receiving region and the aerosol generator.

12. A device as in claim 10, wherein the feed system housing includes a top portion and a bottom portion having the tapered bottom end, wherein the top portion is attachable to the bottom portion to permit the top portion to be removed from the device housing, and wherein the first region and the overflow region each comprise an elongate channel extending through the top portion.

13. A device as in claim 12, further comprising an o-ring seal positioned between the top portion and the bottom portion.

14. A device as in claim 8, wherein the aerosol generator includes a seal member to produce a seal between the aerosol generator and the interface.

15. A device as in claim 8, further comprising a lid coupled to the feed system housing that is adapted to secure the container within the first region.

16. A device as in claim 15, wherein the lid includes a slot that is adapted to receive a top tab that extends from the top end of the container.

* * * * *